United States Patent [19]

Pohler

[11] Patent Number: 4,844,073

[45] Date of Patent: Jul. 4, 1989

[54] DEVICE FOR TREATMENT OF HEMORRHOIDS AND RECTAL TISSUE AFTER SURGERY TREATMENT

[76] Inventor: Jerzy Pohler, 388 NE. 87th St., Miami, Fla. 33138

[21] Appl. No.: 228,834

[22] Filed: Aug. 3, 1988

Related U.S. Application Data

[63] Continuation of Ser. No. 936,362, Dec. 1, 1986, abandoned.

[51] Int. Cl.⁴ .......................... A61F 7/12; F24H 1/10
[52] U.S. Cl. .................................. 128/401; 215/321; 220/306
[58] Field of Search ............... 128/385, 399, 400–403, 128/303.12, 341, 343; 604/43; 215/320, 321; 220/356, 306, 307

[56] References Cited

U.S. PATENT DOCUMENTS

| | | | |
|---|---|---|---|
| 2,873,881 | 2/1959 | Nichols | 220/306 |
| 4,014,456 | 3/1977 | Echtle | 220/306 |
| 4,235,349 | 11/1980 | Uhlig | 220/306 |
| 4,418,833 | 12/1983 | Landis | 220/306 |
| 4,444,332 | 4/1984 | Widen et al. | 215/321 |
| 4,487,326 | 12/1984 | Uhlig | 215/320 |
| 4,563,182 | 1/1986 | Stoy et al. | 128/401 |

FOREIGN PATENT DOCUMENTS 2416881  3/1976  Fed. Rep. of Germany ...... 128/401

Primary Examiner—Richard C. Pinkham
Assistant Examiner—Mark S. Graham
Attorney, Agent, or Firm—Richard C. Litman

[57] ABSTRACT

A two-piece rectal insert containing a coolant fluid. The rectal insert includes a one-piece tube for holding the fluid and a one-piece cap which seals against the tube. The tube and the cap have complementary sealing structures to prevent the coolant fluid from leaking from the insert. The cap has a ring to which a string is tied. The string is pulled to remove the insert from the rectum. The cap and a wing portion of the tube provide a stop to prevent the insert from going too far into the rectum.

2 Claims, 2 Drawing Sheets

U.S. Patent Jul. 4, 1989 Sheet 1 of 2 4,844,073
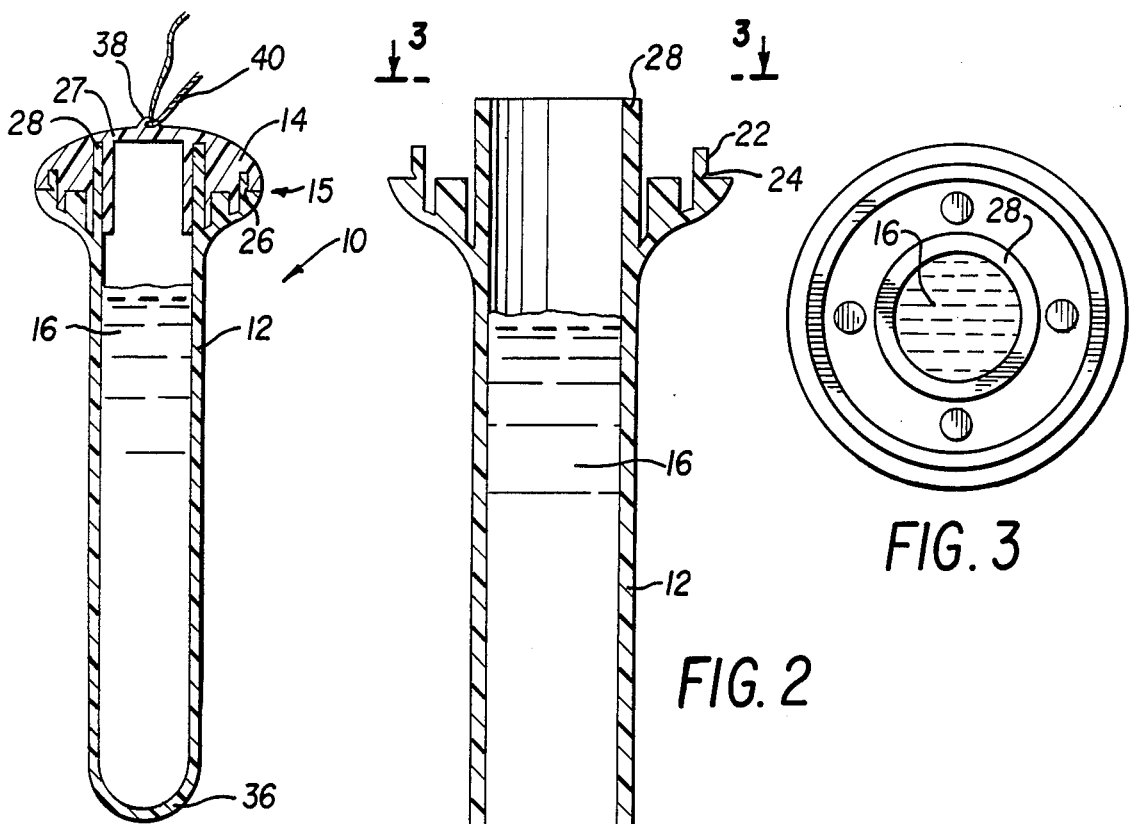
FIG. 1
FIG. 2
FIG. 3
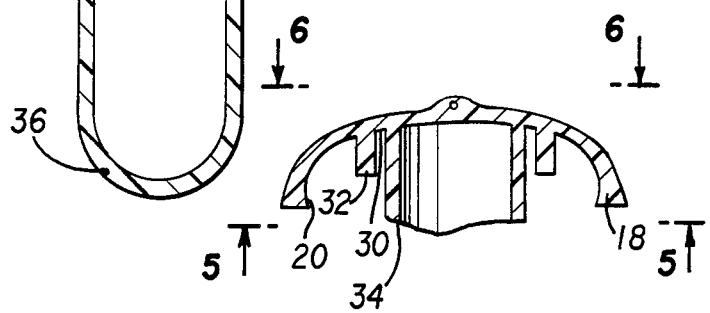
FIG. 4
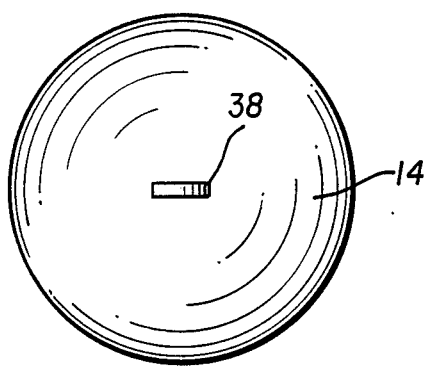
FIG. 6
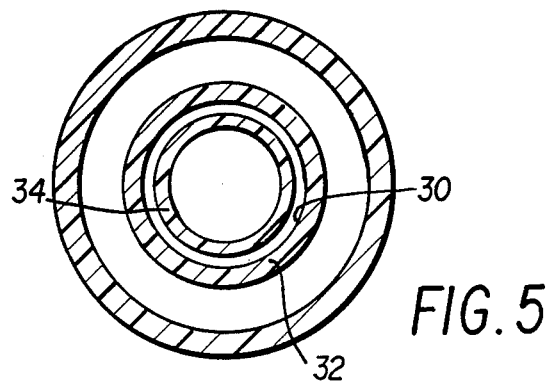
FIG. 5

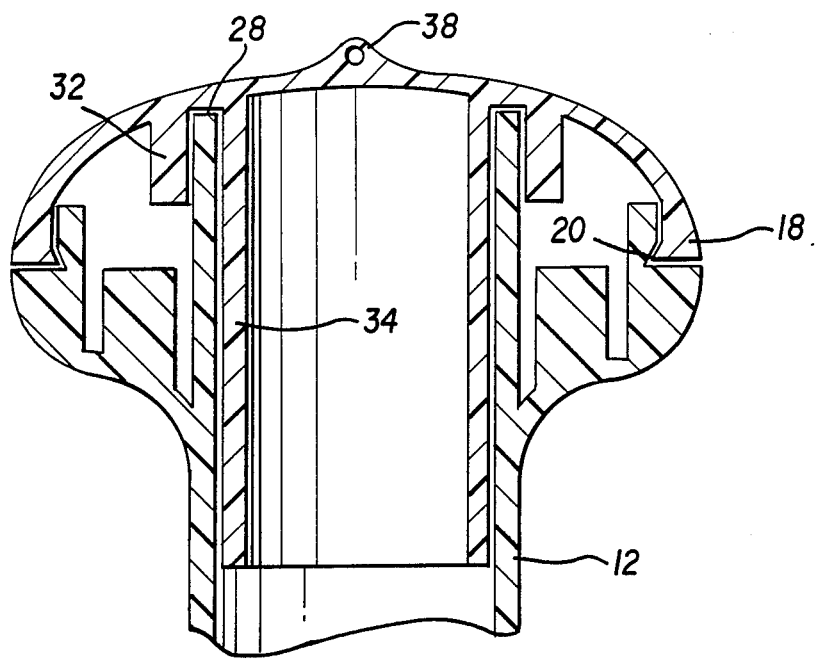
FIG. 7
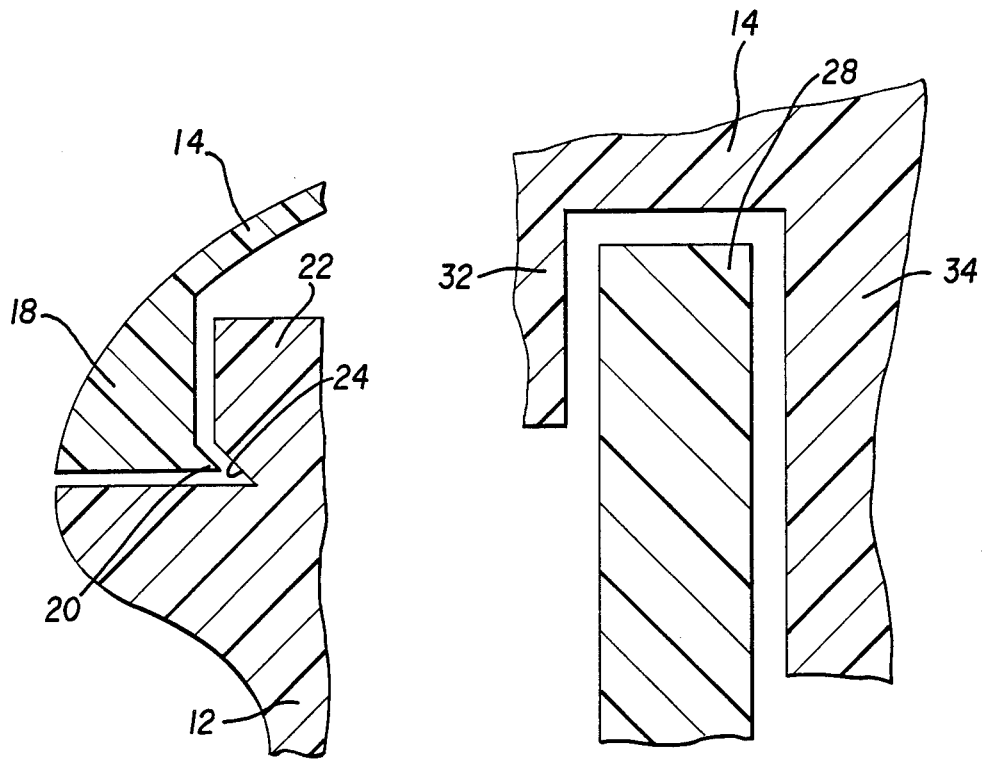
FIG. 8
FIG. 9

DEVICE FOR TREATMENT OF HEMORRHOIDS AND RECTAL TISSUE AFTER SURGERY TREATMENT

This is a continuation of co-pending application Ser. No. 936,362 filed on Dec. 1, 1986 now abandoned.

BACKGROUND OF THE INVENTION

A. Field of the Invention

Many approaches have been made to the treatment of hemorrhoids and rectal tissue following surgical procedures over the years with varying degrees of success in each case. One approach has been the use of a cold temperature rectal insert for treating the hemorrhoids and to promote healing process after surgery. It is to this field of invention that the present invention is desired.

B. Prior Art Found in the Field of the Invention

The closest prior art located in the field of the invention is described in U.S. Pat. No. 3,939,842 issued to A. M. Harris and in U.S. Pat. No. 4,563,182 issued to V. M. Stoy et al. The Harris patent discloses a unitary molded plastic rectal insert encapsulating a freezable liquid comprised of water, ethylene glycol, propylene glycol and mixtures thereof. The insert is fabricated from low density polyethylene tubing that is extruded with varying wall thicknesses and then blow molded, filled and then sealed.

The Stoy et al patent discloses a rectal insert comprised of a meltable hydrogel. The hydrogel contains from 35-90% water and is frozen into a desired rectal insert shape in a blister pack. Then the hydrogel insert is removed from the blister pack and inserted directly into the rectum. As body heat is conducted into the hydrogel, the hydrogel melts thereby losing its physical shape. The hydrogel is without physiological effect on the user.

Another patent, U.S. Pat. No. 3,885,403 issued to J. J. Spencer relates to a hot and cold compress which maintains its solid state, usually a frozen state, over a wide temperature range. This device is employed externally to contact the skin of the user and donate prolonged cold to the external area impacted. The pad is essentially a tough, flexible envelope containing a liquid or paste or gel which has a low freezing point and a high boiling point. The envelope contains a gelling agent such as carboxy vinyl polymer of high molecular weight, and a water/glycol mixture exhibiting freezing point depression characteristics. The envelope is used as a hot or cold compress to be laid flat against the skin of the user to heat or cool the external skin surface.

A problem associated with a one piece rectal insert containing a frozen liquid mixture comprised of toxic materials such as ethylene glycol and propylene glycol is that there is danger of causing injury to the user if the insert springs a leak.

Another problem associated with prior art rectal inserts is that they are sometimes difficult to remove after they have been in position for a period.

A problem associated with a rectal insert comprised of a hydrogel that melts in direct contact with body tissues is that the melted hydrogel creates an undesirable mess. Furthermore, as the hydrogel melts, it loses its physical shape causing an undesirable sensation of a rectal insert having a constantly changing shape and size.

There is a need for a simple rectal insert having provisions to avoid leaking of confined fluids. There is also a need for a rectal insert which provides for easy removal after use. There is a need for composition to act as precooling (frozen) media to provide/obtain sufficient period of cooling time.

BRIEF SUMMARY OF THE INVENTION

Accordingly, the invention which comprises the subject matter sought to be patented in this application comprises an improved rectal insert having special leak prevention structures and having a provision for ease of removal of the insert after use.

The rectal insert of the invention is an article of manufacture comprised of two pieces. One piece is a cap, and the other piece is a tube. The cap and tube have complementary interlocking sealing structures to prevent a coolant fluid confined within the insert from leaking out. Preferably, the tube is a one-piece article of manufacture.

In accordance with another aspect of the invention, the cap and the tube together form a lateral winged top element which prevents the rectal insert from being inserted too far into the rectum.

In accordance with still another aspect of the invention, the cap is provided with a small annular ring through which a string can be inserted and secured. By pulling the string attached to the insert, the insert can be easily removed.

BRIEF DESCRIPTION OF THE DRAWINGS

FIG. 1 shows a longitudinal cross sectional view of one embodiment of the invention.

FIG. 2 shows a longitudinal cross sectional view of a tube element of the embodiment of the invention shown in FIG. 1.

FIG. 3 is an overhead view of the tube taken along the lines 3—3 in FIG. 2.

FIG. 4 is a cross sectional view of the cap element of the embodiment of the invention shown in FIG. 1.

FIG. 5 is a bottom view of the cap taken along the lines 5—5 in FIG. 4.

FIG. 6 is an overhead view of the cap taken along the lines 6—6 in FIG. 4.

FIG. 7 is an enlarged partial cross section of the top portion of the rectal insert in FIG. 1.

FIG. 8 is an enlarged fragmentary view of structure shown in FIG. 7.

FIG. 9 is an enlarged fragmentary view of further structure shown in FIG. 7.

DESCRIPTION OF THE PREFERRED EMBODIMENTS OF THE INVENTION

Referring to FIG. 1 of the drawing, a rectal insert 10 of the invention includes a tube 12 and a cap 14 contoured at the surface of their junction to be smoothly continuous in change of curvature in all directions in the vicinity of the junction and also, otherwise, to be smooth all over the tube 12 and cap 14, so as to be resistant to contamination. A coolant fluid 16 is contained in the tube 12. The cap and the tube together form a lateral winged stop element 15 which prevents the rectal insert from moving too far into the rectum.

Also referring to FIGS. 2-5, multiple complementary sealing structures are provided on the tube and the cap to prevent the fluid 16 from leaking out of the rectal insert. The cap has a distal annular lip 18 having an acutely angled or inturned edge 20 which engages an outer projection 22 on the tube 12. The outer projection 22 of the tube has an annular groove 24 on its outer wall 22 which is complementary to edge 20 and is engaged thereto to form a first seal 26 for preventing the fluid 16 from leaking out of the rectal insert. The engagement between the groove 24 on the tube and the acute edge 20 on the cap also serves to secure the cap to the tube. In this respect, the acute edge 20 of the cap snaps into engagement with the groove 24 on the tube. For enlarged views of the first seal 26, see FIGS. 7 and 8. Increased efficacy in the first seal 26 may be had if the complementary sealing structures are dimensioned so that they form a tight fit with one another. For purposes of clarity, the sealing components are shown in exploded relationship in FIGS. 7-9.

Another second sealing structure 27 is provided between the top rim 28 of the tube and a complementary groove 30 on the cap. The groove 30 on the cap is formed between middle cylindrical projection 32 and inner cylindrical projection 34. The middle cylindrical projection 32 engages the outer wall 12' of the tube 12, and the inner cylindrical projection 34 engages the inner wall 12" of the tube 12. To assure provisions of an effective second sealing engagement 27, the inner cylindrical projection 34 projects into the tube 12 for a distance approximately equal to the height of the lateral winged stop 15. Increased efficacy in the second seal may be had if the complementary sealing structures are dimensioned so that they form a tight fit with one another. For enlarged views of the second seal 27, see FIGS. 7 and 9.

For providing the second sealing structure 27, an alternative sealing structure may be used. Complementary threads on the tube 12 and the cap 14 may be used to provide a seal 27 between the cap and the tube.

The tube 12 has a rounded end 36 which facilitates insertion into the rectum. Preferably, the end 36 would be greased to further facilitate insertion.

The basic idea behind the present method of hemorrhoid and rectal tissue following surgical treatment is to provide a cold contact tube 12 brought into proximate tactile relationship with swollen distended rectal tissue. The contact with cold serves to lessen the sensations of pain and also serves to bring about vasoconstriction in the rectal tissue. When conducted for a reasonably protracted period of time, say five to ten minutes duration, such contact relieves the symptoms of the malady for several hours and grants temporary symptomatic relief to the hemorrhoidal suffer.

The tube 12 is kept cold by means of coolant fluids 16 placed inside the tube. The coolant liquid is capable of being frozen solid; and once in this condition it holds this state for a prolonged period of time because of its chemical compositions. The frozen coolant 16 thaws to 37 degrees C or body temperature within about eight minutes of contact with rectal tissue. The effect generated by such tissue contact lasts for three to six hours and can be repeated several times each day since such contact does not damage or harm the tissues.

The rectal insert of the invetion may be a disposable unit that is disposed of after one use. Alternatively, the rectal insert of the invention may be refrozen prior to a subsequent use. To freeze or refreeze the rectal insert of the invention in a conventional household freezer takes approximately 4 hours.

Another aspect of the invention relates to the ease with which the rectal insert can be removed after use for a period of time. A small annular ring 38 is located at the top center of the cap 14. A string 40, as shown in FIG. 1, is threaded through ring 38 and secured thereto. When it is desired to remove the insert from the rectum, the string 40 is pulled, and the insert is removed thereby. In this way, the hand of the person does not need to become soiled when the rectal insert is removed. Preferably, the cap 14 and the ring 38 are formed as a one-piece article of manufacture.

In general, the rectal insert of the invention may be used once or twice a day for as long as desired. The level of application frequency will depend in large measure on the patient. Should the patient elect to employ the rectal insert twice daily once in the morning and once in the evening, he or she should experience protracted relief within seven days from the outset of treatment. If relief does not occur, then it is generally the case that other more complicated factors are involved and a physician should be consulted.

By using the rectal insert of the invention, no chemicals are applied to human tissues. The tube 12 is impervious to passage of the contained coolant 16. The tube may be fabricated from polyvinyl chloride, high density polyethylene, or high density polypropylene resins which are rapid conductors of heat or cold but will not permit migration of liquid or vapors therethrough.

The coolant fluid 16 may be composed of the following ingredients in the amounts specified:

| Ingredient | Percent by Weight |
|---|---|
| Aqueous Gel (Blue Ice) Non-Toxic, Non-Poisonous | from 60 to 80% |
| Distilled Water | from 40 to 20% |

Density of the composition to increase cooling time may be varied as suits the need of the occasion so long as it performs the function of sufficient delay in release of its tissue cooling and vasoconstricting effect on the rectal hemorrhoidal tissue for sufficient length of time.

While the foregoing example serves to illustrate to those versed in the art the preferred mode of practice of the invention sought to be patented herein, reference can be made only to the several appended claims for legal definition of the scope of the invention sought to be patented.

What is claimed:

1. A two-piece rectal insert adapted to contain a fluid coolant comprising;
    an elongated tube having a closed rounded end and an opposite open end bounded by a top rim,
    winged stop means integral with said tube radially extending from the external periphery of said tube and axially spaced a substantial distance from said open end rim,
    a unitary cap attachable over said tube open end rim to retain fluid coolant in said tube, pull means on the center of said cap to permit removal of the insert from the rectum,
    disparate first and second sealing and interlocking means attaching said cap about said tube open end and preventing leakage of fluid coolant from said tube,
    said first sealing and interlocking means including an annular distal lip on said cap contoured at the junction of said tube and said cap smoothly with a continuous change of curvature in all directions in the vicinity of said junction, said distal lip having an inturned edge, a cylindrical outer projection on said stop means having an outer wall and projecting axially in the direction of said tube open end, an annular groove at the base of said wall, said cap lip concentrically engageable about said stop means outer projection with said cap inturned edge adapted to snap fit within said stop means annular groove, said second sealing and interlocking means disposed radially inwardly of said first sealing and interlocking means and including an inner cylindrical projection on said cap closely insertable within said tube open end and axially extending substantially past said stop means, a middle cylindrical projection on said cap axially extending concentrically of said inner projection and defining an intermediate annular groove therebetween adapted to tightly receive said tube top rim whereby, attachment of said cap to said tube provides a fluid tight insert with dual, disparate sealing and interlocking components co-joined in a firm manner.

2. A two-piece rectal insert according to claim 1 wherein, said cap pull means includes a ring, and a flexible cord attached through said ring.

* * * * *